United States Patent
Glater

(12) 
(10) Patent No.: US 6,461,287 B1
(45) Date of Patent: Oct. 8, 2002

(54) CENTRIFUGAL VACUUM CONCENTRATOR AND MODULAR STRUCTURED ROTOR ASSEMBLY FOR USE THEREIN

(75) Inventor: Michael Glater, Brooklyn, NY (US)

(73) Assignee: Thermo Savant Inc., Holbrook, NY (US)

( * ) Notice: Subject to any disclaimer, the term of this patent is extended or adjusted under 35 U.S.C. 154(b) by 0 days.

(21) Appl. No.: 09/358,525

(22) Filed: Jul. 22, 1999

(51) Int. Cl.⁷ ................................................. B04B 5/02
(52) U.S. Cl. .............................. 494/16; 494/13; 494/61; 494/34; 494/83; 159/DIG. 11
(58) Field of Search ................................ 494/43, 83, 12, 494/13, 20, 34, 61, 84, 60, 16; 422/72, 177; D24/219; 436/45; 159/6.1, DIG. 16, DIG. 11; 202/238

(56) References Cited

U.S. PATENT DOCUMENTS

| | | | | |
|---|---|---|---|---|
| 2,907,663 A | * | 10/1959 | Parkinson et al. |
| 3,304,990 A | * | 2/1967 | Ontko et al. |
| 3,720,368 A | * | 3/1973 | Allen |
| 4,017,354 A | * | 4/1977 | Marchenko et al. |
| 4,412,831 A | * | 11/1983 | Avery et al. |
| 4,708,940 A | * | 11/1987 | Yoshida et al. |
| 5,084,133 A | * | 1/1992 | Guy et al. |
| 5,242,370 A | * | 9/1993 | Silver et al. |
| 5,674,173 A | * | 10/1997 | Hlavinka et al. |
| 5,741,397 A | * | 4/1998 | Kraver |

FOREIGN PATENT DOCUMENTS

JP          62225202     * 10/1987

* cited by examiner

Primary Examiner—Joseph W. Drodge
Assistant Examiner—Terry K. Cecil
(74) Attorney, Agent, or Firm—Darby & Darby

(57) ABSTRACT

A large capacity centrifugal vacuum concentrator includes a rotor assembly mounting a plurality of vertical spaced rotors mounted on a drive shaft and intervened with spacers between each lower rotor and a rotor next above, the rotors and spacers having interengaging drive transmission means for transmitting drive to the rotors and spacers when the drive shaft is driven. The rotor assembly is enclosed by a, e.g., cylindrical stainless steel cover which sits on a base and with the base defines a vacuum chamber. When the cover is elevated to open position, four quadrant access is available for loading and unloading of samples on the rotors. The rotor assembly is made up of interchangeable rotors, spacers and vessel holder frames which are selected from families of such dependent on particular vessel capacity and holder frame requirements.

44 Claims, 8 Drawing Sheets

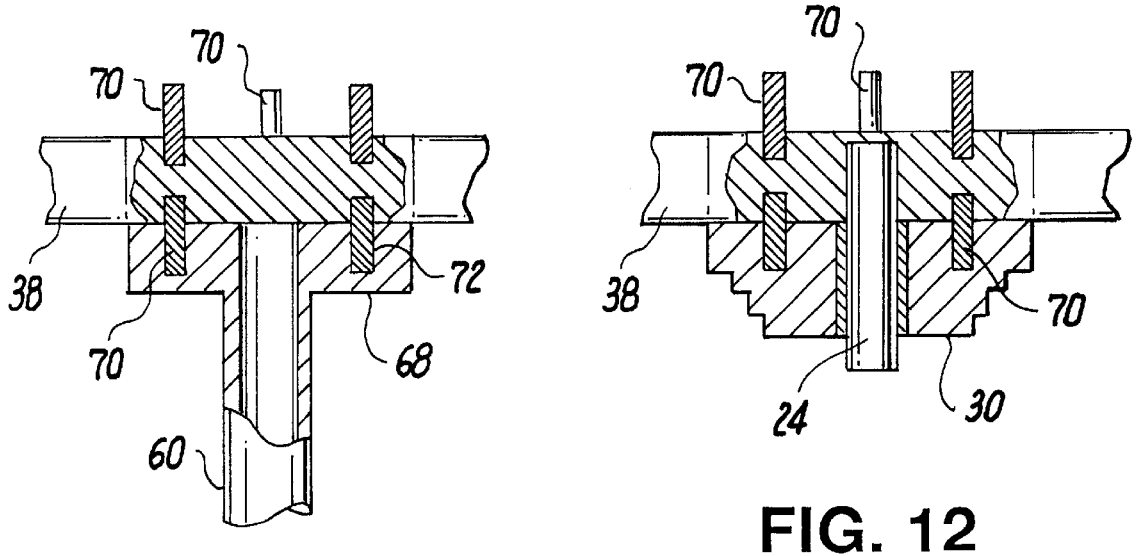
FIG. 11
FIG. 12
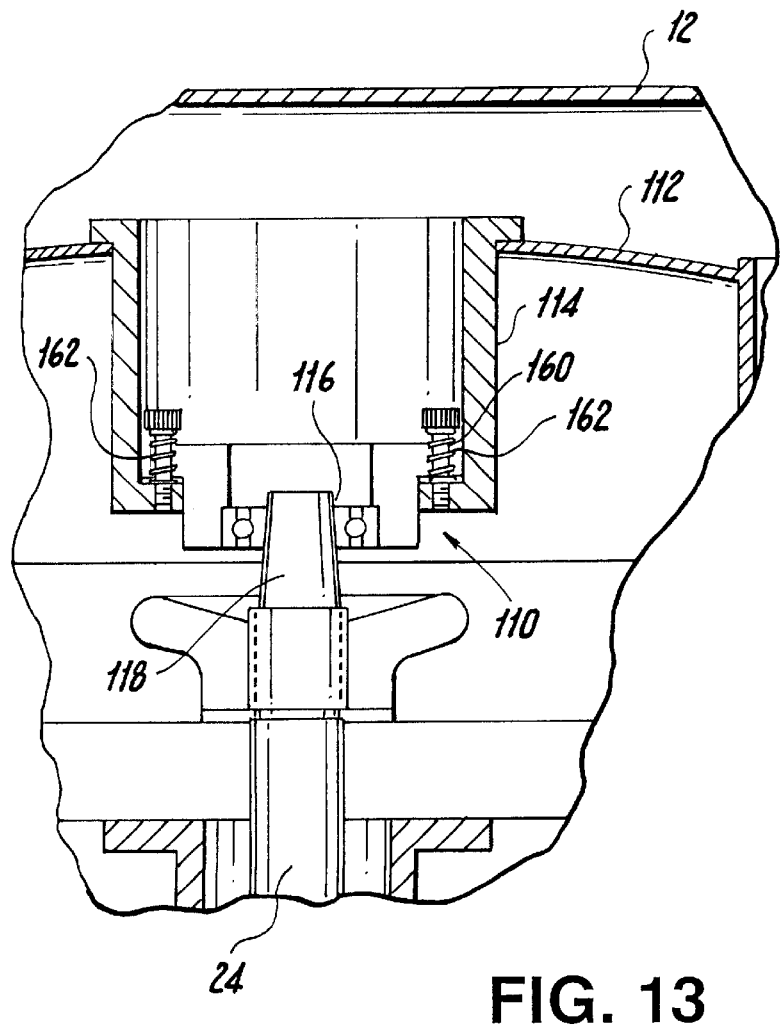
FIG. 13

CENTRIFUGAL VACUUM CONCENTRATOR AND MODULAR STRUCTURED ROTOR ASSEMBLY FOR USE THEREIN

BACKGROUND OF THE INVENTION

The present invention relates to a centrifugal vacuum concentrator and more particularly to large capacity concentrator for concentrating or drying large numbers of samples in the same concentrator in a single operation. These samples can be biological, drug, environmental or analogous materials wherein the material to be recovered by drying is suspended or mixed in a liquid.

The invention also relates to a modular rotor assembly which can be assembled from families of modular components involving use of numbers and types of rotors, rotor spacers and vessel holders required for a particular sample drying operation and scale, the modular rotor assembly readily being reconfigurable from a given assembly form to another assembly form wherein different capacity and numbers of rotors, spacer sizes and sample vessels and the holders therefor are used.

Generally where samples of biological or drug materials such as DNA, RNA etc are to be recovered they will be contained in a liquid or solvent vehicle. The liquid sample is in or is placed in a vessel such as a tube, the tube being mounted on a rotor of the rotor of the concentrator. The rotor can mount plural vessels, e.g., fifty or more. In one known concentrator arrangement, tubes are received in bore passages of the rotor located circularly spaced about the rotor, the bore passages being inclined upwardly and radially toward the rotor center so that during rotor high speed rotation, sample "bumping" is inhibited.

The concentrator, e.g., that described in commonly owned U.S. Pat. No. 4,226,669, is closed to seal the vacuum drying chamber, the rotor is started up and brought up to the required high speed, and the vacuum pump is turned on to evacuate the drying chamber and maintain a prescribed condition of vacuum therein. Under such conditions vaporization of the liquid in which the sample material is contained proceeds and continues until the liquid is fully vaporized and the sample material dried. Heat such as from lamps in the drying chamber can be supplied to facilitate drying.

There has developed a need to process very large numbers of samples such as drug discovery samples. In some research facilities, it is known to have to screen many thousands of samples each month. To meet the demand this creates for high capacity concentrator capability, a vacuum centrifugal concentrator has become available wherein two or three rotors are provided, the rotors being superposed one above another. Further, various forms and capacities of sample vessel holders can be used on the rotors to increase the numbers of sample vessels useable in a single drying operation.

A drawback of these known high capacity concentrators is the difficulty of accessibility to the rotors for loading and unloading of sample vessels. The rotors are situated in a housing wherein space between the rotors and the containment housing inside wall surfaces is limited. In one known concentrator, access to the scientist/technician for loading and unloading operation is from above the rotor. This is not especially disadvantageous as to the circumstance of there being only one large rotor used but if a second below rotor was used, it would be tedious and difficult to have to work around and under an upper rotor when loading or unloading a rotor beneath.

In another known concentrator, plural rotors are housed in a rectangular casing. One side of the casing is provided with a casing height door so that alongside access is available to each rotor. But this access is only as to part of the rotor periphery. To access rotor locations remote from the door, the rotors have to be hand rotated to bring the remote part to the access side of the housing.

The confined chamber space character of these known concentrators also makes them less than satisfactory in regard to servicing components of the concentrator within the chamber such as heaters and in respect of cleaning the interior of the concentrator. An additional and significant consideration is the possibility of a scientist/technician injuring a hand when manipulating same in the chamber in association with the tasks noted above.

A shortcoming of known high capacity concentrators is that same are purpose built in regard to the numbers and constructions of rotors that are used therewith and, while to a lesser extent, the types, numbers and arrangements of vessel holders on the rotors. In other words, it is not possible with the known types to have a character of interchangeabilty allowing altering a concentrator capacity need by adding or removing rotors or using rotors of different configurations especially as such configurations lend to most efficient arrangement of certain ones of vessel holders than others.

OBJECTS AND SUMMARY OF THE INVENTION

Accordingly, it is an object of the invention to provide a centrifugal vacuum concentrator which overcomes the drawbacks of the prior art.

It is a further object of the invention to provide a centrifugal vacuum concentrator with a capacity for drying large numbers of samples in a single operation.

Another object is to provide a centrifugal vacuum concentrator which has the flexibility for drying samples mounted in sample vessels of diverse construction and sample capacity.

A further object is to provide a centrifugal vacuum concentrator which is constructed such that access for loading and unloading sample vessels on the rotors is optimized in that such access is available from all of four quadrants of an imaginary circle whose center is on the rotor axis insuring that quick simple loading/unloading tasking is possible.

Another object is to provide a centrifugal vacuum concentrator which allows clear easy unobstructed access to the space about the rotor assembly for cleaning and maintenance purposes as well as the inner part of the concentrator cover which is elevated clear of the rotor assembly when in open position, this thereby making cleaning, maintenance and other tasks easily and safely carried out.

A still further object is to provide a vacuum centrifugal concentrator modular rotor assembly which is comprised of interchangeable rotors, rotor spacers and sample vessel holders selected from families of such components which thereby allows simple and quick alteration of concentrator capacity for drying samples dependent on types and quantities of the samples which are to be dried.

Another object is to provide a modular rotor assembly for a centrifugal vacuum concentrator which can be pre-assembled and stored at a location proximal the concentrator for quick simple installation when a concentrator drying capacity requirement must be changed on shift over from one protocol of drying to another different protocol involving different numbers and sizes of samples being dried.

Briefly stated, there is provided a large capacity centrifugal vacuum concentrator which includes a rotor assembly mounting a plurality of vertical spaced rotors mounted on a drive shaft and intervened with spacers between each lower rotor and a rotor next above. The rotors and spacers have interengaging drive transmission means for transmitting drive to the rotors and spacers from the drive shaft when it is driven in rotation. The rotor assembly is enclosed by a cover, e.g., a cylindrical stainless steel vessel which sits on a base and with the base, defines a vacuum chamber. When the cover is elevated to an open position, four quadrant access is available for loading and unloading of samples on the rotors. The rotor assembly is made up of interchangeable rotors, spacers and vessel holder frames which are selected from families of such components dependent on particular vessel capacity and holder frame requirements.

In accordance with these and other objects of the invention, there is provided a centrifugal vacuum concentrator for concentrating liquid samples contained in sample vessels comprising a base on which a rotor assembly is mounted. The rotor assembly includes a drive shaft upright and rotatable on the base about a fixed axis, and a plurality of rotors is on the drive shaft spaced one above another each at a corresponding one of a plurality of locations above the base, Each rotor carries sample vessel holding structure. A cover is received on the base, the cover having a closed position wherein it surroundingly encloses the rotor assembly and defines with the base an operating chamber. The cover in closed position thereof engages with the base such as to establish an air excluding seal of the operating chamber with respect to an outside air environment. The cover has an open position wherein the cover is disengaged from the base and unobstructedly located relative to the base such that alongside at rotor level access is user available from locations in each of four quadrants of an imaginary circle the center of which lies on said fixed axis for mounting and demounting sample vessels from the rotor sample vessel holding structure. Means is provided for communicating the operating chamber with a source of vacuum.

The access to the sample holder structure from all quadrants when the cover is open is in a circular course of at least about 330 degrees.

An elevator unit, e.g., a lead screw drive unit, can be used to raise and lower the cover between closed and open positions, such unit being effective to elevate the cover to an open position wherein the cover lowermost part is above a topmost rotor in the assembly.

Means are provided to communicate the chamber with a source of vacuum. The vacuum source can be a vacuum pump housed in the base. Communication of the chamber with the vacuum pump can be by way of an opening in the base communicating with a pump inlet.

A fitting can be located in a head of the cover and be communicated to a fume hood and fume removal operation by a flexible hose to allow removal of noxious and harmful vapors emitted during sample drying and before the cover is opened with lab personnel in the proximity.

Heaters such as tubular heaters encircling an outer periphery of the cover wall can be provided on the cover to heat the chamber, these being mounted vertically spaced on the cover so as to supply heat energy into the chamber in a manner as promotes uniform heat condition in the chamber. Further, one or more lamp heaters can be mounted on the cover wall structure and on a head of the cover to direct heat energy at the rotor levels where the samples are located to promote drying of same. Further a heater can be provided in the base.

Drive means for rotating the drive shaft can be located in the base. The rotors are loosely received on the drive shaft and each lower rotor in the assembly is intervened by a spacer also loosely received on the drive shaft. The spacers set the spacing on the drive shaft between the several rotors mounted thereon. Coupling structure on the rotors is cooperative with coupling structure on the spacers for driving coupling these components to the drive shaft for rotation therewith. This coupling structure can be projections on one of the spacers and rotors and passages or openings in the other of said spacers and rotor in which the projections engage. The drive means can have a drive output with which the lowermost rotor engages with coupling structure, e.g., as aforesaid to effect the transmission of rotary drive to the rotor assembly through the lowermost rotor.

The sample vessel holding structure on each rotor comprises one or more holding frames which can be selected from a family of holding frames of differing holding capacity removably fixable to the rotor. The holding frames receive and hold one or more vessel holders in which sample vessels inclusive of vials, tubes, etc are received.

The invention provides that a lower end of the drive shaft is supported on the base, while the upper end is removably received in a self-centering bearing assembly carried at the underside of the head. This upper end of the drive shaft freely inserts into and removes from the bearing when the cover is closed and opened, respectively.

It is provided that the spacers in the rotor assembly are of a common length set of such selected from a family of differing common length sets. By employing selected ones of the sets, the spacing between rotors is altered and a more or less number of rotors will be in the assembly. In these circumstances, the heights of vessel holders and containers received therein can correspondingly be altered to fit rotor spacing and access requirements.

Use of a family of spacers as well as different configurations of rotors provides an interchangeabilty capability to the rotor assembly for changing the capacity of the concentrator to suit a particular requirement within a spectrum of less rotors with use of large size vessel holders and large capacity sample vessels to a use of more rotors with use of small capacity vessel holder such as stacked microtitre plates.

Other features of the invention provide that a variable speed drive motor can be used, and viewing windows be present in both the cover and outer casing so that a strobe light device mounted at convenient location on the cover head can be projected onto sample vessels so that volume level of samples can be monitored. The strobe light also can be used for checking rotor speed.

According to a feature of the invention, there is further provided a modular structured rotor assembly for mounting to a drive unit of a centrifugal concentrator. This rotor assembly comprises a drive shaft, and a plurality of rotors loosely received on the drive shaft and spaced along the shaft at a succession of rotor locations. Tubular spacers loosely received on the shaft intervene a face of a rotor in the succession and an opposed face of a rotor next following in the succession with each of opposed ones of spacer ends in contact with said face and opposed face. Means are provided for holding the rotors and spacers in urged together relationship on the drive shaft as a longitudinal assemblage. Coupling means are provided for unitarily coupling together each spacer and rotor to the drive shaft for effecting rotation of said spacers and rotors in unison with the drive shaft.

The modular structured rotor assembly is configured to be removably received in a base drive unit in driving relationship with a rotary output member of such unit.

The tubular spacers can be a set of common length spacers selected from a family of differing common length sets of spacers. The selected spacer length sets the spacing between rotors in the succession and the rotors can be color coded differently for each common length set to facilitate assembly.

With a modular structured rotor assembly, it is possible to pre-configure a number of rotor assemblies each intended for a specific capacity and drying sample requirement. Since the rotor assembly components for each specific requirement already are set up, it remains only to lift the unwanted rotor assembly from the base and substitute that needed.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 11 is a fragmentary elevational view partly in section of the rotor/spacer cooperative engagable structure for drivingly coupling together each rotor and an adjacent spacer;

FIG. 12 is a fragmentary elevational view partly in section depicting the manner of coupling a lowermost rotor in the assembly with a drive output member of the drive means in the base so as to transmit rotary drive to the rotor assembly;

FIG. 13 is a fragmentary elevational view, partly in section, showing the mounting of a rotary drive shaft upper end supporting free floating bearing housed in the cover head.

DETAILED DESCRIPTION OF THE PREFERRED EMBODIMENT

Figure 1:
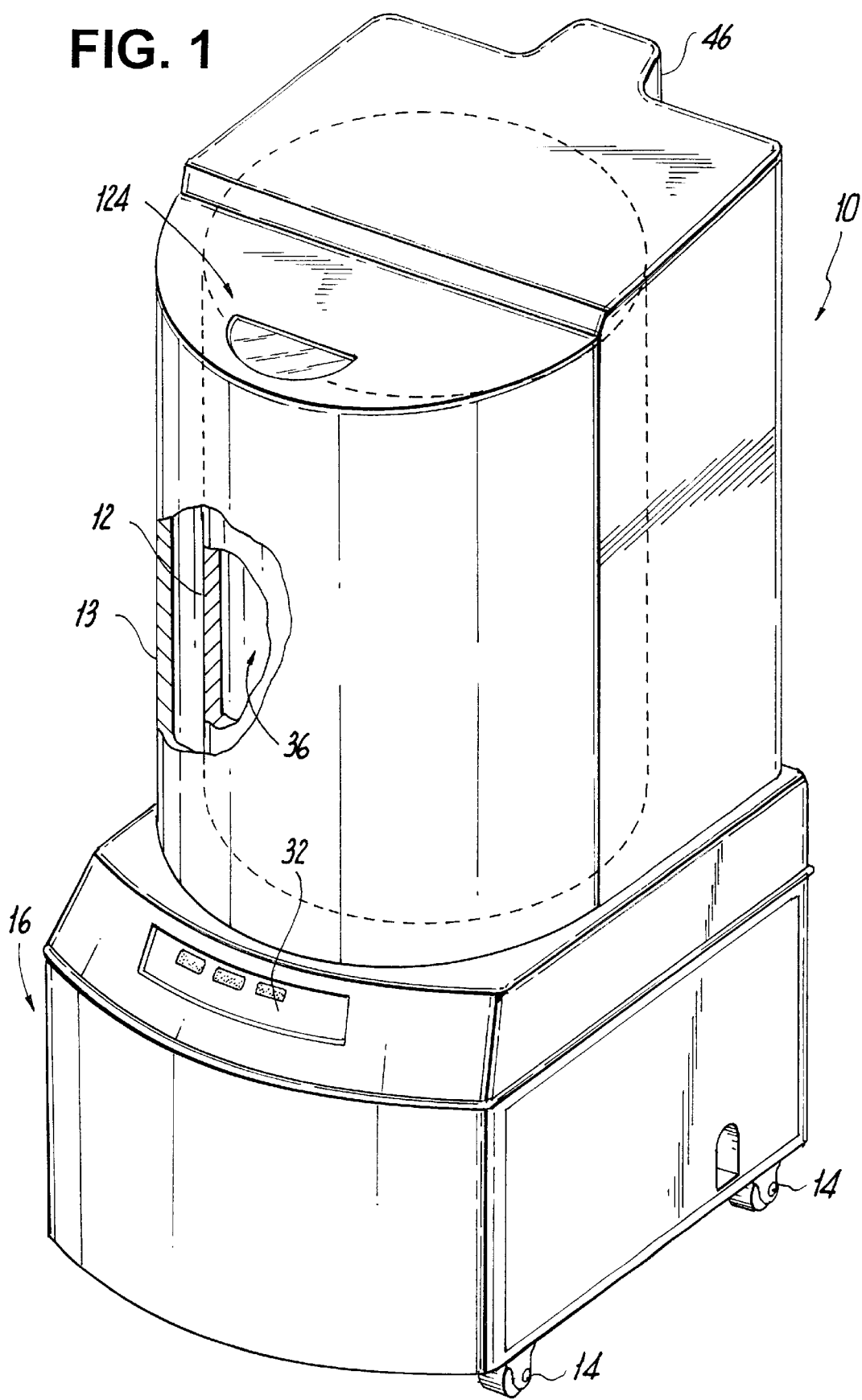
FIG. 1 is a perspective view of a centrifugal vacuum concentrator constructed in accordance with the invention with the cover closed in which condition the cover is set on the base in an air excluding seal relationship therewith and thus defines a vacuum chamber in which drying takes place, the cover being seen in dashed lines within an outer decorative casing that enshrouds the cover.
Figure 2:
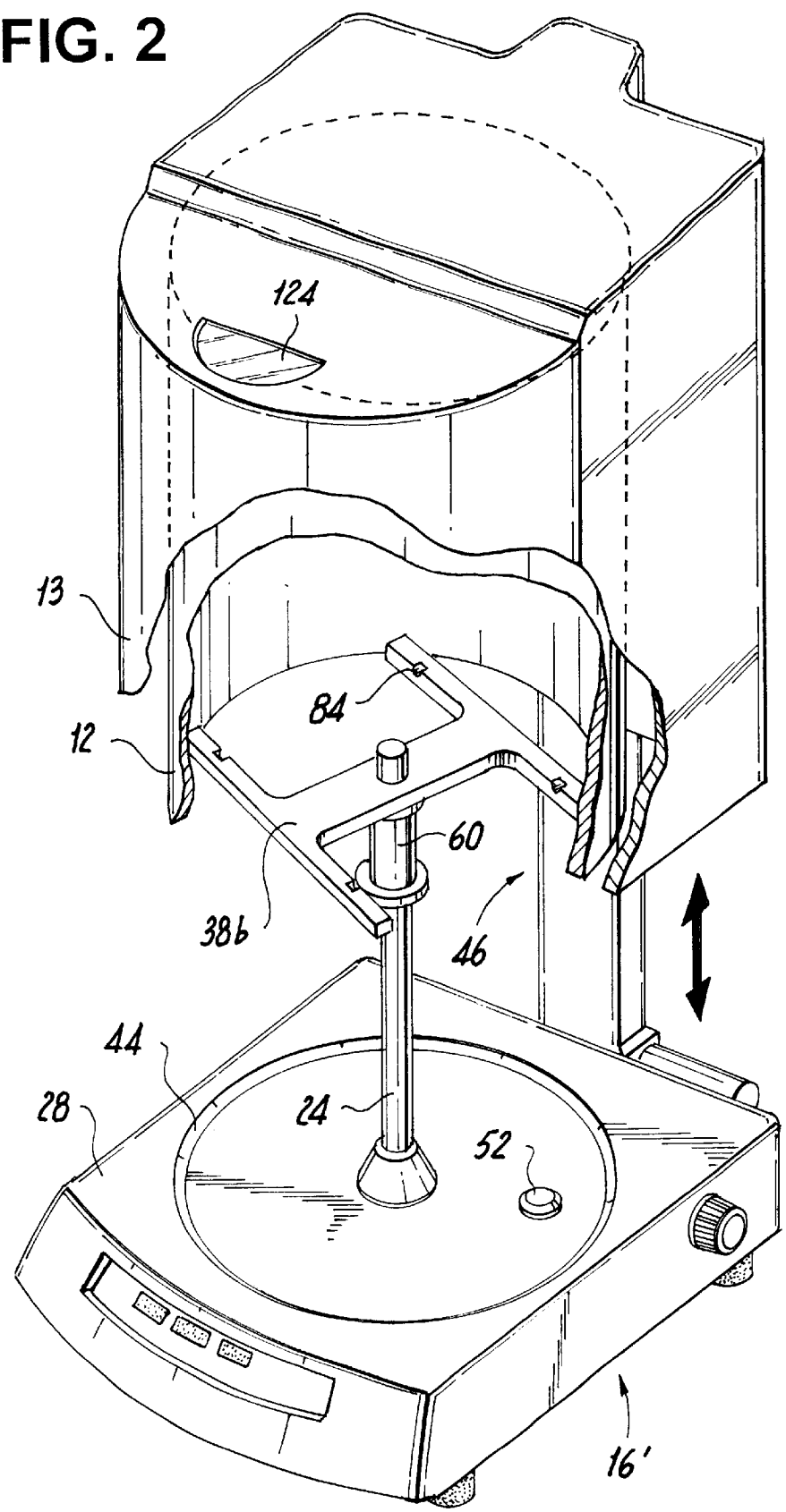
FIG. 2 is a perspective view of the concentrator with the cover and outer casing moved to open position with portions of the cover and outer casing broken away for purpose of depicting details of the rotor assembly mounting on the base, for convenience only an uppermost rotor and the spacer immediately thereunder being shown and without any holding frame being fixed to the rotor, the base being a modified embodiment of that shown in FIG. 1.
Figure 3:
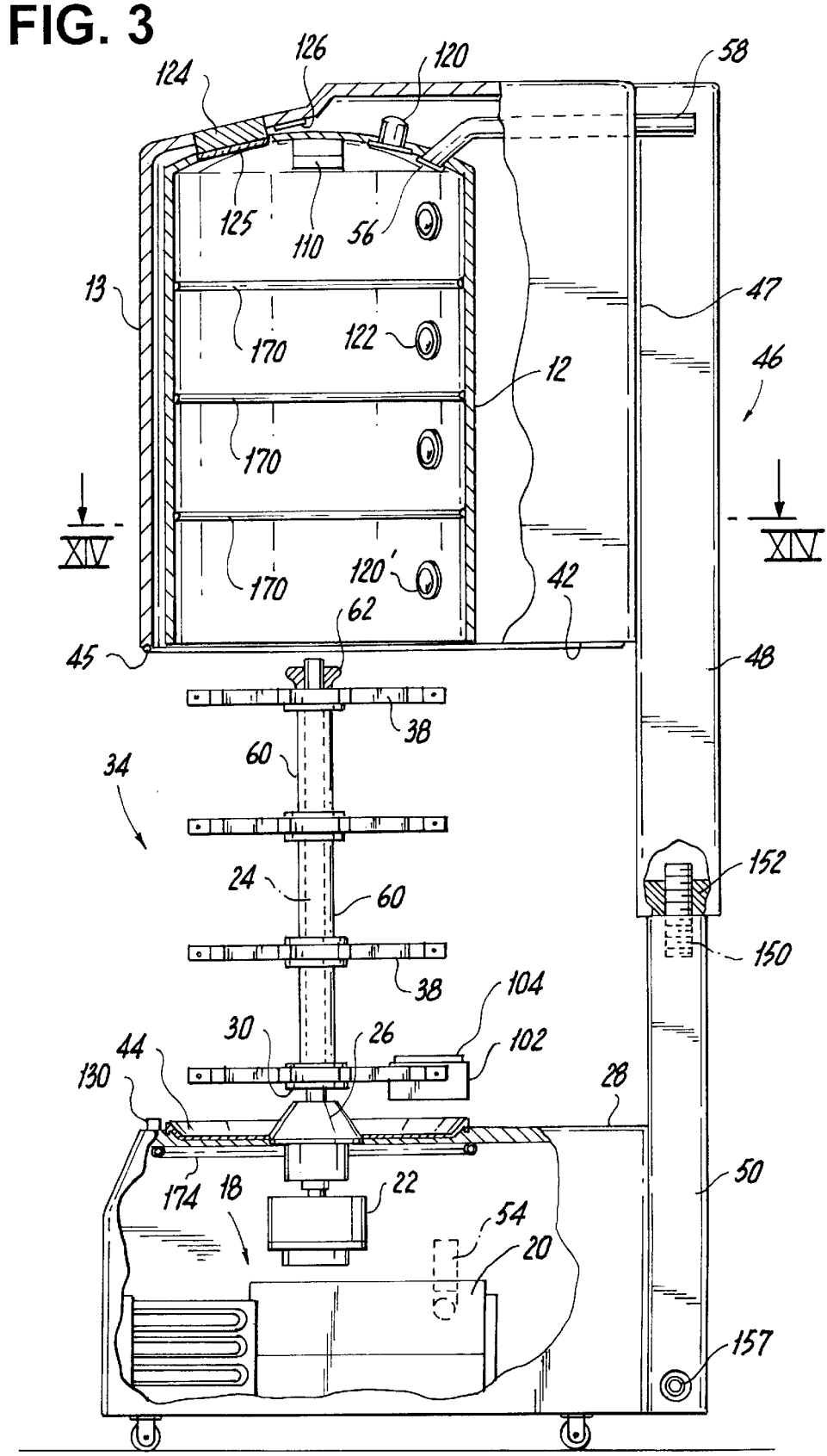
FIG. 3 is a side elevational view of the FIG. 1 concentrator with the cover and outer casing shown in raised open position, a side wall of the base being removed so that various components housed in the base can be seen, and a single one only of the holding frames which can be carried on the rotors for holding sample vessel holders being depicted.
Figure 4:
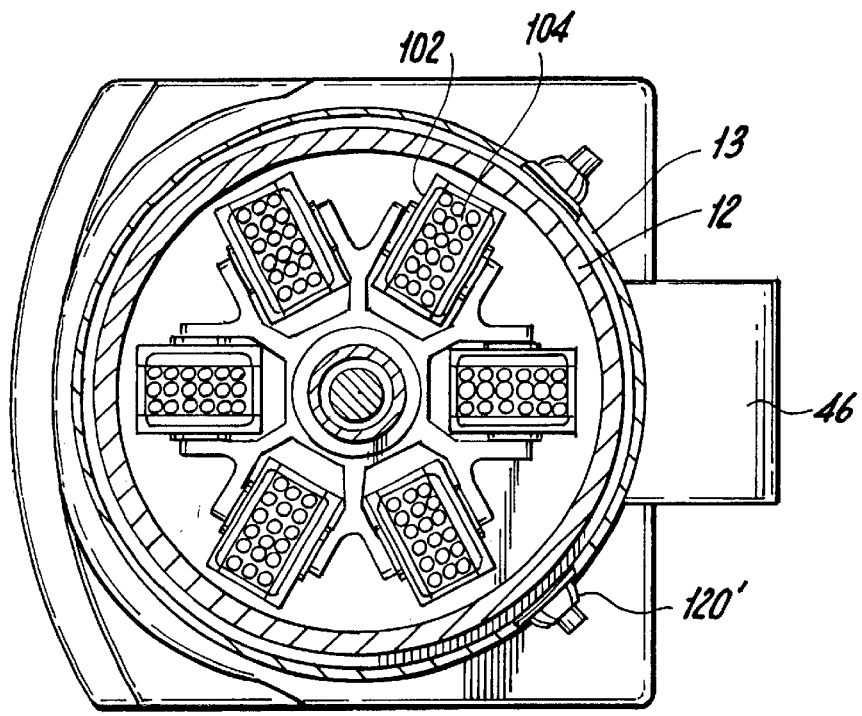
FIG. 4 is a top plan view of the concentrator with the cover top head and the top part of the outer casing removed so as to depict a manner of mounting sample vessels holders in holding frames carried by the rotors, the sample vessel holders receiving plural sample vessels.

Referring to FIGS. 1–3, there is depicted a centrifugal vacuum concentrator 10 intended for use in a research or commercial testing laboratory. The concentrator 10 commonly will be sited at one use location in the laboratory. Further, in an actual embodiment it will occupy a floor space of about 3×3 feet and require overhead clearance of about 8 and ½ feet with the cover 12 in open position as seen, e.g., in FIG. 3. However, the concentrator 10 can be equipped with caster wheels 14 to facilitate moving it about to another location and/or moving it, e.g., as may be required when mounting or demounting of a concentrator modular rotor assembly in manner as will be described later.

Cover 12 is a cylindrically configured, heavy walled vessel open at the bottom and having a top head 112. The cover serves to enclose the space herein later defined as the vacuum chamber. Cover 12 desirably will be made of corrosion resistant metal such as stainless steel. As noted from FIGS. 1–3, a decorative casing 13 enshrouds cover 12, its inner surfaces being spaced but several inches from the outer periphery of the cover 12. As is explained later, casing 13 is mounted to move up and down in tandem with cover 12 during opening and closing of the concentrator. It is to be understood though that casing 13 other than being fitted with a viewing window 125 for reason as will be given later, serves aesthetic purpose only.

The concentrator 10 includes a base 16 wherein is housed certain components such as a refrigerant compressor, condenser, cold trap, controls etc, these being noted generally at 18 in FIG. 3. The components also include a vacuum pump 20. The use and functioning of the components aforesaid are well known to a person skilled in the art for which reason more elaborate description herein is not needed or given herein except where thought necessary. Base 16 also houses an electric, preferably a variable speed, motor powered rotary drive unit 22. This rotary drive unit 22 rotates upright placed drive shaft 24, the drive shaft 24 passing through a vacuum sealing gland at the top of the base, and can include a housing 26 above a base top 28, this housing being surmounted by a disc-shaped drive output member 30.

Base 16 includes a front side instrument panel 32. The base 16' (FIG. 2) is a variant base form being somewhat squatter than that shown in FIGS. 1 and 2 and illustrated as not being fitted with caster wheels.

Drive shaft 24 mounts an assembly of rotors 38 shown generally at 34. With the cover 12 in the FIG. 1 closed position, the cover surroundingly encloses the rotor assembly 34 and defines with base top 28, an operating chamber 36 wherein the concentrating or drying of samples occurs, this being carried out while the chamber 36 is maintained under influence of a condition of vacuum.

With cover 12 in closed position, its lower encircling edge 42 sits in a seal member 44 at the top of base 16. The character of the engagement of said lower encircling edge 42 with the seal member is such as to establish during drying, an air excluding seal of vacuum chamber 36 preventing incursion of any outside ambient air to the operating chamber so the chamber when under vacuum remains so.

Opening and closing of the cover 12 can be effected in various ways. One such way is to use an elevator unit shown generally at 46 in FIGS. 1 and 3. The elevator unit includes a movable standard 48 telescoped over a fixed standard 50. The upper part of movable standard 48 is fixed to a rear part 47 of the cover. It also is fixed to a rear part of the decorative outer casing 13 so that casing 13 and cover 12 raise and lower in tandem. Elevating means such as a hydraulic cylinder can be used to motivate upward travelling movement of standard 48.

An advantageous form of elevator unit drive uses a lead screw 150 carried and operable in standard 50 and cooperating with annular internal screw fitting 152 fitted in standard 48. Rotation of lead screw 150 raises and lowers the cover. Use of the lead screw type unit allows that if an electric power failure occurred in a laboratory so that the motor drive of the lead screw was rendered inoperable with the cover closed, the lead screw could be operated by hand cranking the motor drive unit to raise the cover so that irreplaceable samples could be saved, such being effected with a hand crank 157 located at the base of the elevator unit.

Elevating will be to an open position extent wherein the lower encircling edge 42 of the cover 12 when the cover is open, is located above any sample vessel held in sample holder structure of an uppermost rotor in the rotor assembly so that immediate convenient access for loading and unloading of sample vessels as well as assembly and disassembly of rotor components is available. It is understood that the outer decorative casing 13 also has a lower encircling edge 45 and it too locates above any sample vessel in the sample holder structure on elevating of the cover 12.

For communicating the chamber 36 with a source of vacuum, a number of ways can be employed for such purpose. As seen in FIG. 2, an open fitting 52 can be set in the base 16 and be in communication through a base interior pipe 54 with an inlet of the vacuum pump 20.

Referring to FIG. 3, a fitting 56 can be mounted in the inside of the head of the cover 12 and connected with a flexible vacuum hose 58 that can be led to a fume hood operation for removing noxious fumes from the chamber. The flexible hose would be of length to accommodate opening and closing movements of the cover 12.

Referring again to FIGS. 2 and 3, the rotor assembly 34 mounted on the drive shaft 24 will comprise a plurality of two or more rotors 38 carried on the drive shaft in vertical spacing one above another. The lowermost rotor will be proximal the base 16. Where three or more rotors 38 are used in the assembly, each lower rotor will be uniformly spaced from the rotor 38 next above by a spacer 60.

Spacers 60 in the assembly will comprise a common length set of tubular spacers and be selected from among a family of sets of common length spacers wherein the respective sets are of differing lengths, these in turn being employed on the basis of the number of rotors 38 to be used which in turn will have relation to the sample vessel numbers and sizes necessary for a particular concentrator drying requirement capacity. Use of common length sets of spacers and of different configurations of rotors provides an interchangeability utility to the concentrator for quickly changing over concentrator capacity from one to another over a range of capacities. Further, this interchangeability availability provides for utilization of a modular structured rotor assembly made up to a specific capacity need and installable as a unit on the base in place of a prior installed different capacity unit. Description of such modular structured rotor assembly will be given later.

Regarding the interchangeability feature of the spacers, the spacers of each common length set can be color coded in a color different than any other common length set thereby to facilitate make up of a needed capacity rotor assembly.

Figure 6A:
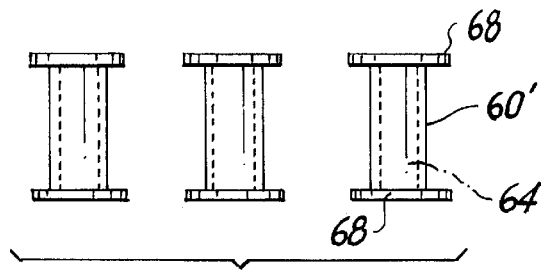
FIGS. 6(a)–6(c) are elevation showings of a number of sets of spacers in a family of spacers which can be used in the concentrator.
Figure 6B:
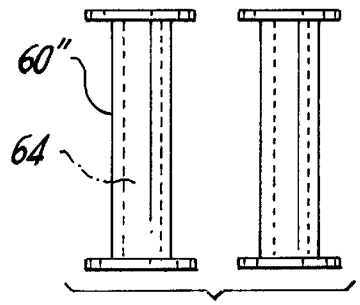
Figure 6C:
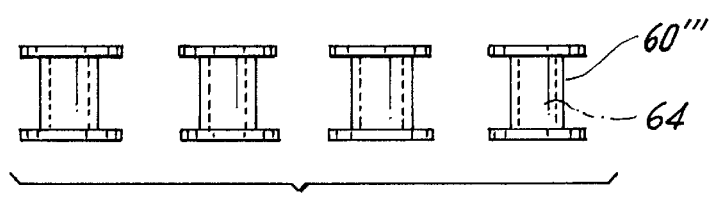

Thus and referring to FIGS. 6(a)–(c), if four rotors are to be mounted in the assembly, the spacers 60' of the FIG. 6(a) set of spacers and three in number will be used. If three rotors are to be used, selection will be of two spacers 60" of the FIG. 6(b) set. If concentrator capacity requirement involves use of five rotors, four spacers 60''' of the FIG. 6(c) set will be used. In a circumstance where but two rotors 38 would be mounted in the assembly, spacer selection would involve not only need for the one such for spacing the lower rotor from the upper rotor but also need for a tubular component (not shown) extending above the upper rotor to a location wherein the locknut 62 (FIG. 3) tightly engages therewith to hold the assembly in longitudinal (i.e., axial) fixed assembly on the drive shaft 24.

Spacers 60 are tubular members loosely closely received on drive shaft 24 via through bore passages 64. The rotors 38 also are loosely received on the drive shaft 24 via central through bores 66 (FIGS. 9 and 10), and closely encircle the drive shaft. The spacers as best seen in FIGS. 6(a)–6(c), can have annular flanges 68 at each of opposite spacer ends. Since the rotors 38 and spacers 60 are loose on drive shaft, coupling means for coupling together these components in driving relationship with the drive shaft is required and such will be described next.

FIGS. 11 and 12 depict respectively, the coupling together in diving relationship, each rotor 38 and spacer 60 adjacent therewith, and the coupling of the lowermost rotor 38 to the drive shaft 24 so that such rotor will be driven from the drive shaft and in turn transmit rotary drive to the remaining and located above assembly rotors and spacers. This coupling conveniently is effected with cooperating structure on the several components to be coupled in the form of projections on a one component and passages or openings on a other component with which the projections mate.

With reference to FIG. 11, (each) rotor 38 carries at both its upper and its lower face a number of projections 70. As seen from FIGS. 9 and 10, the projections can be four in number although three or more than four also could be used. The projections 70 will be symmetrically arrayed on the rotor faces spaced around the rotor bore 66. The spacer 60 will be provided in its flanges 68 with companion passages 72 in number and array correspondence to the rotor projections 70 so that the projections are received in the passages establishing a tandem codirectional rotary driving relation therebetween. Depending on the wall thickness of the spacer tube, it could be provided without flanges and the passages 72 formed directly in the spacer wall structure. Further, a reversal of arranging projections on the spacer and passages in the rotor could be used although is not as preferred as the use of projections on the rotor and passages in the spacer.

Rotary driving of the rotors and spacers in unison with the drive shaft 24 is effected as seen in FIG. 12 with a coupling of the drive shaft to at least one of the rotors or spacers or but preferably it need only be done to a lowermost rotor of the assembly. In other ways, a disc fixed to the shaft could interpose between a spacer flange and a rotor face. Projections on a rotor could pass through the disc and into passages in the spacer flange.

As seen in FIG. 12, projections 70 at the bottom face of the lowermost rotor are received in passages or openings in exteriorly located rotary output member 30 of the rotary drive unit 22, said arrangement of output member on the base 16 being shown in FIG. 3. With this coupling, lowermost rotor 38 rotates with the drive shaft 24 and in turn, each coupled together spacer and rotor above the lowermost rotor is driven by rotation of the lowermost rotor 38.

Figure 9:
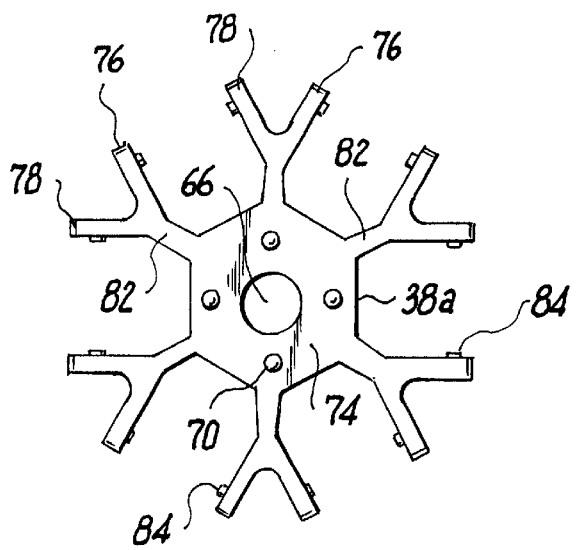
FIG. 9 is top plan view of one form of rotor used with the concentrator and in the modular structured rotor assembly.
Figure 10:
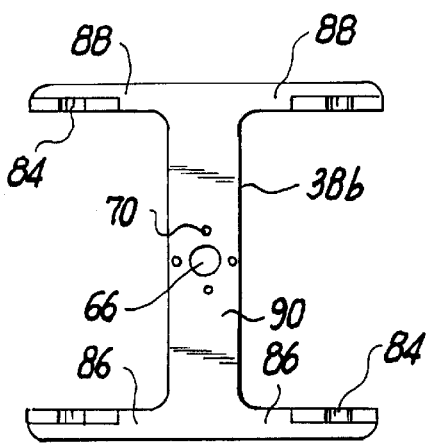
FIG. 10 is a top plan view of another form of rotor useable with the concentrator and with the rotor assembly.

FIGS. 9 and 10 depict several different configurations of the rotor types useable in the concentrator. The FIG. 9 rotor 38a has a center hub body part 74 from which extends a number of radial branches 82 which bifurcate into divergent support arms 76, 78. These divergent arms are symmetrically and so arrayed about the rotor center axis that each support arm 78 of one branch 82 is parallel spaced to and paired to a 76 arm of an adjacent branch 82. These parallel spaced support arms 78, 76 cooperate to define a cradle for reception of a sample vessel holding means. The sample holding means will be described later but it is noted such holding means will be supported pivotably by these support arms and the support arms can be fitted with pivot support members 84 for that purpose.

The FIG. 10 rotor 38b has two pairs of symmetrically arranged parallel arms 86, 88 extending from a diametrical center bar 90. Each pair of support arms 86, 88 cradles a sample vessel holding means in a pivotable mounting of such means, and these arms include pivot support members 84 to which sample vessel holding means will be fitted.

With regard to the sample vessel holding means, reference is made to FIG. 3 wherein one such holding means, e.g., a basket 102 is shown in place on the lowermost rotor 38. The holding means also can be a frame or other like receptacle suited to hold one or more vessel holders 104 representative ones of such vessel holders being depicted in FIGS. 8(a)–8(c). The vessel holders 104 receive and hold sample vessels and/or in some instances, the samples themselves.

Figure 5:
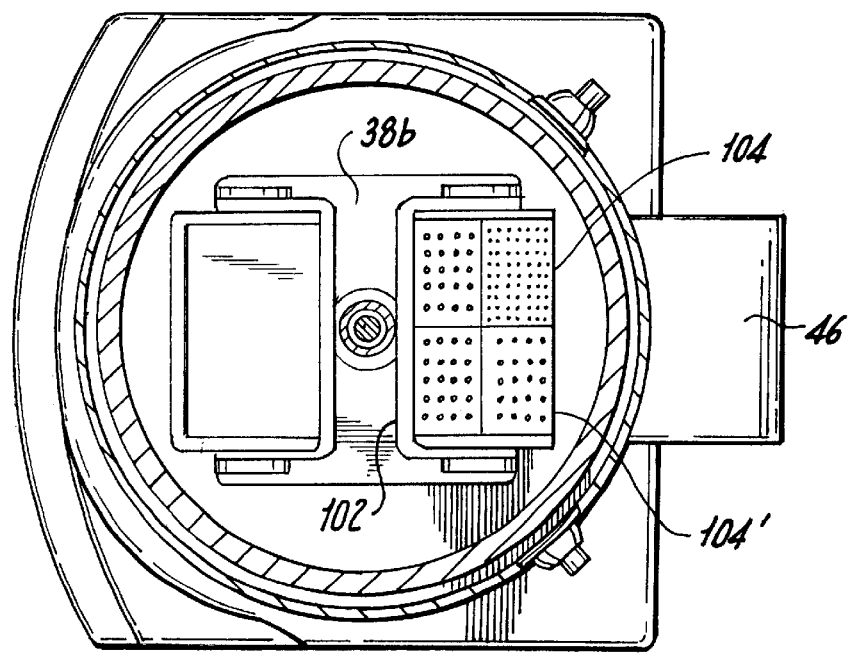
FIG. 5 is a view similar to FIG. 4 except the, holding frames and sample vessel holders are ones selected from different ones of the sets of such as are depicted in FIG. 4.
Figure 8A:
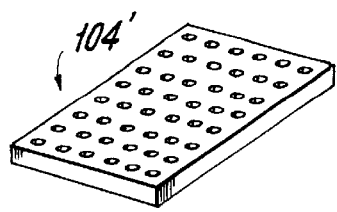
FIGS. 8a–8c are perspective showings of representative types of sample vessel holders which can be used in the concentrator.
Figure 8B:
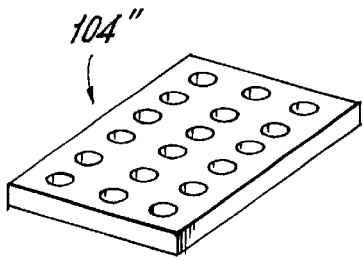
Figure 8C:
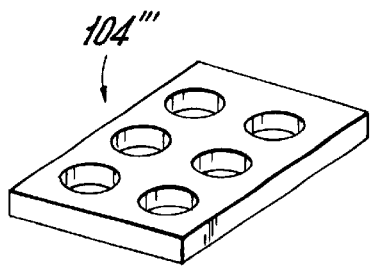

Referring to FIG. 8(a) vessel holder 104' is a microtitre plate capable of holding up to 96 samples in separate wells. These holders commonly will be used in a stacked plurality, e.g., a stack of five such plates. In the FIG. 5 embodiment, it is seen that four stacks of microtitre plates 104' can be received in each basket, two such baskets being mounted on each rotor type 38b. FIG. 8(b) depicts another vessel holder 104'' which is employed for holding tube vessels which can, e.g., hold 18 tubes. FIG. 5 illustrates that each of the baskets 102 support one of the vessel holders 104'', there being six such holders at each level of rotors 38a. FIG. 8(c) shows another vessel holder 104''' for holding very large sample tubes. Depending on rotor and basket configuration, one or more of such holders could be mounted in a basket 102.

The loading and unloading of sample vessels task associated with the large capacity of inserting and removing vessel holders must be carried out by the researcher or technician with care so as to prevent spilling a sample from a sample vessel or dropping of a sample vessel out of its holder or even dropping the holder itself. Also, with the known concentrator type, tightness of space for accessing the vessel holders can make the task very arduous. Entry removal access space to the concentrator interior for the loading and unload work is at most from one of plural housing sides and with a smaller sized opening in said side. If a top opening access be provided, even more difficulty could be encountered if plural rotors are use since to loading and unloading of one rotor beneath another rotor would be most difficult. The concentrator of the invention presents no such problems to the user for reason as discussed next and with reference to FIG. 14.

Figure 14:
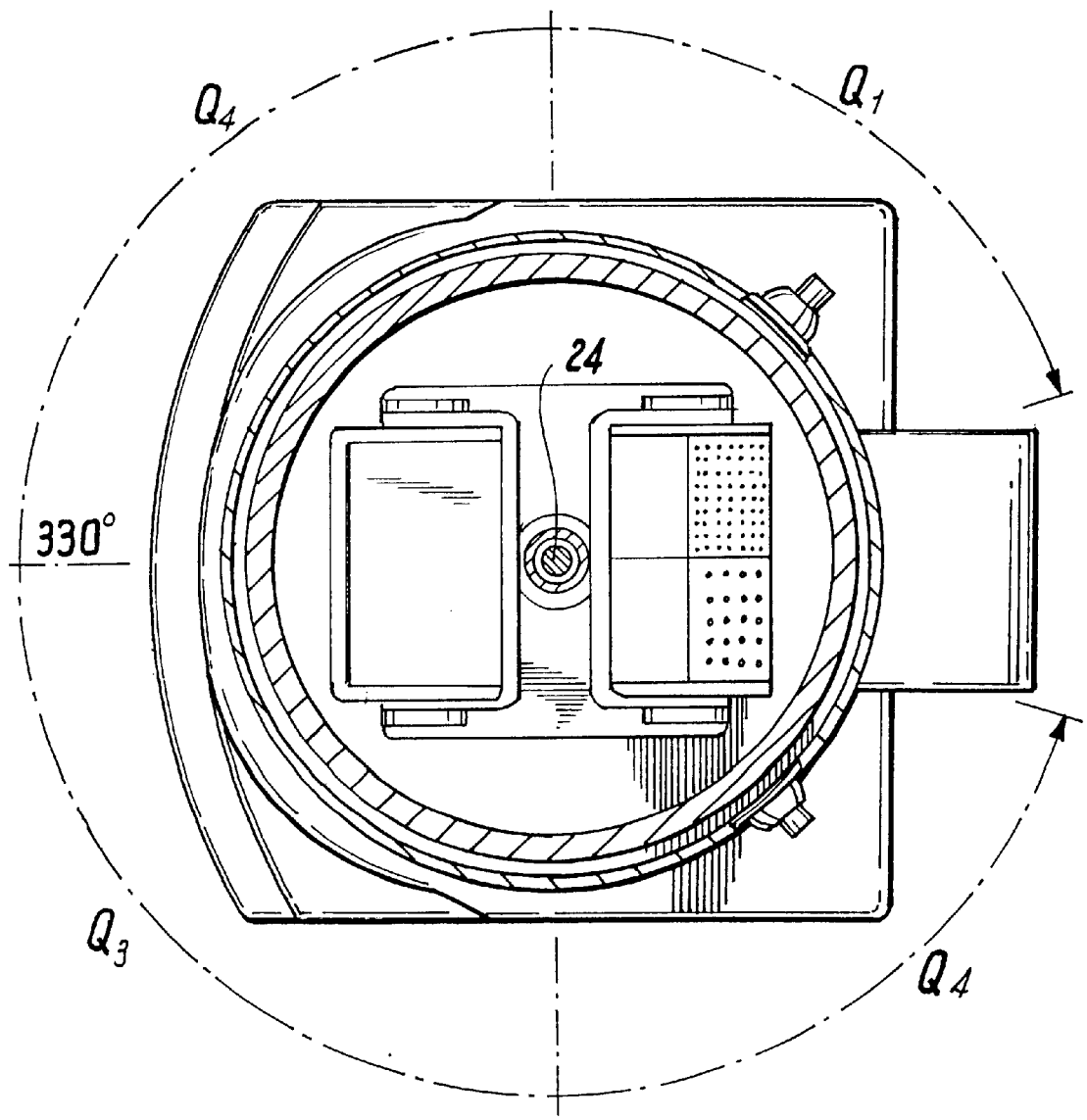
FIG. 14 is a horizontal section view through the concentrator taken along line XIV—XIV in FIG. 3 to illustrate the circumferential range of four quadrant access to mounting and demounting of specimen vessels incident use of the concentrator.

For sample loading and unloading of the concentrator, the cover 12, which has a generally circular plan configuration at least as to its chamber defining inner structure, is elevated to the FIG. 3 open position. In that condition, all rotors and hence, all baskets 102 and vessel holders 104 are accessible in a range of locations extending substantially all around same and at the horizontal level where placement or removal of vessel holders is needed. As seen in FIG. 14, this range of access is extends through all four quadrants of an imaginary circle the center of which lies on the fixed axis about which drive shaft 24 rotates. The extent of this range is an arc of at least about 330 degrees as seen in FIG. 14 and it extends through the depicted four quadrants Q-Q. Limitation on access is present only at the location of the elevator unit 46 located at the rear side of the cover 12 and casing 13.

FIG. 13 shows the manner of operationally supporting the upper end of drive shaft 24. When the rotor is operating at the high RPM's involved in sample drying, it is necessary to properly give upper end support. For that purpose, a self-centering bearing assembly 110 is carried in the top or head 112 of cover 12. A saddle 114 depends from head 112 and in turn carries a floating ball bearing unit 116 fixed therein, the bearing unit being secured to the saddle with screws 160.

Compression springs 162 encircle the shank of the screws 160 and engage at opposite ends thereof with the underface of the screw heads and an upper flange face of the saddle. The compression springs 162 exert vertical loading on the bearing unit normally to level it but yet allow tilt thereof as when a shaft upper end is entered in the bearing to assure that any slight off alignment of the mating is compensated for by the freedom of the bearing to tilt to accommodate reception of the shaft upper end properly aligned in the bearing inner race.

The upper end of the drive shaft is tapered as at 118. With the cover in descended closed position, the said tapered end 118 is in engagement with the inner race of the ball bearing which is companion tapered to the drive shaft upper end. When the cover moves down from open position, the tapered arrangement and self-centering nature of the ball bearing allows the ball bearing which also is moving down to find and properly seat with the shaft end to give full bearing support. When the cover is moved upwardly to open position, the bearing simply slides upwardly away from the shaft upper end.

As is common with centrifugal vacuum concentrators, concentrator 10 carries heaters to provide drying promoting heat energy to the drying chamber 36. Referring to FIG. 3., tubular electric heaters 170 are carried on the outer side of the wall of cover 12 and encircling same at locations selected to facilitate heating proximal rotor and hence sample locations in the chamber 36. Heaters 170 preferably will be controlled as a unit during operation. Other heaters 120' like the heater 120 in head 112 can be provided in the wall structure of the cover and individually controlled. FIG. 3 shown a line of heater connect fittings 122 extending down the cover wherein heaters 120' can be mounted to direct heat to the chamber. Further, a tubular heater 174 can be mounted at the upper surface of the base 16, e.g., in an annular groove recess in the base. The heater numbers and arrangements is provided so as to establish uniform heating condition in the chamber 36.

As seen in FIGS. 1 and 3, a viewing window 124 is provided at the front side of casing 13. Another viewing window 125 is provided in the head of cover 12, the two viewing windows being aligned so that an observer can look down into the chamber 36 during a drying operation. A reason for such is for checking sample level in the sample vessels during drying. To allow this, a strobe unit 126 can be mounted in the head 112 of the cover adjacent window 125 and be positioned to direct a strobe light beam onto sample vessels from which sample level in a vessel can be seen. It also is possible to use the strobe light to determine rotor speed.

A safety device arrangement is provided to preclude injury to a user during movement of the cover 12 from open to closed position wherein the user has a body part such as head, hand etc in the path of the descending cover. For such purpose, a beam detector 130 can be mounted on the cover/base as depicted in FIG. 3. If a user's body part is within or crosses the envelope of the cover 12 as it descends, the beam will be broken and such event used to deenergize the elevator unit.

It is contemplated that with use of the lead screw drive for opening and closing the cover, the speed of the lead screw drive motor can be controlled to reduce cover descent to very slow speed in the terminal portion of closing travel. For example, the cover travel speed can be reduced from about one inch per second to about one-quarter inch per second in the last few inches of closure travel before reaching seating on the base. In this way the technician has ample warning and clearance to remove his or her arm and hand from under the cover.

Figure 7:
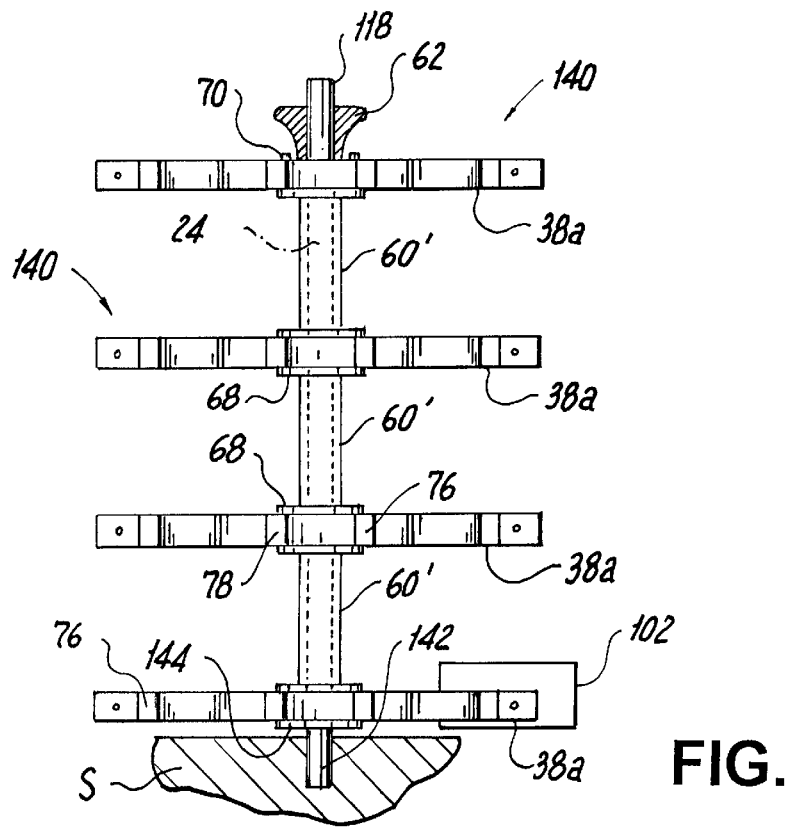
FIG. 7 is an elevational view of a modular structured rotor assembly for mounting to a drive unit of a centrifugal concentrator.

The current mushrooming of research and increase of testing needs has created a corresponding requirement for drying progressively greater numbers of samples in centrifugal vacuum concentrators. The numbers of samples to be dried in a concentrator operation will depend on sample size. This in turn will dictate sample vessel size and such will dictate the type and number of baskets and rotors to be used. Accordingly, drying requirements as to specific sample will be established to maximize the numbers of samples to be carried on the rotor assembly. For enhanced utilization of the concentrator, pre-configured rotor assemblies can be used. Thus, if a first sample type has been dried in an operation and a different second type sample is to be dried, a ready to load pre-configured rotor assembly could be at standby for installation on the concentrator base as soon as the first sample rotor has been removed and the concentrator cleaned. This interchange of rotor assemblies is possible with use of the modular structured rotor assembly of the invention and as will be described next with reference to FIG. 7.

This ability to quickly reconfigure the concentrator from one to another configuration for example, from a pharmaceutical to an environmental configuration has great commercial and scientific advantage and gives the concentrator a drying flexibility not found in known concentrators. Facilitating such flexibility is the use of color coding of the components that can be used by coloring all components for one configuration, e.g., pharmaceutical, one color and all components of another configuration such as environmental, another color. Reconfiguration to specific use is optimized with use of modular rotor assemblies construction of which is given below.

Modular rotor assembly 140 is depicted as having four rotors 38a, a requirement dictated by a particular sample drying requirement. It could have more or less rotors. In making up the rotor assembly, such will be done at a suitable location which could be close by or remote to the concentrator. Also, a mounting stand would be provided present at the location on which assembly of the modular parts into rotor assembly configuration is carried out.

A rotary drive shaft 24M is inserted upright on the stand S, the stand having, e.g., a socket in which can be received a stub end 142 of the drive shaft, this stub end when mounted on concentrator base 16 being drivingly engaged with a drive output from rotary drive unit 22 (FIG. 3).

Drive shaft 24M has a stop such as a disc 144 fixed thereto, this stop serving to support the components being mounted on the drive shaft during assembly. In the FIG. 7 configuration, a first rotor 38a will be loosely received on drive shaft 24M and slid down until its lower face contacts an upper face of disc 144. Disc 144 may be provided with projections which can be aligned with passages in the rotor lower face side so that drive coupling relationship between these components is established.

The rotors are intervened by spacers 60' of the FIG. 6(a) depicted spacers. The spacers have end flanges 68 and the faces of the end flanges are in contact, respectively, with the underface of an above rotor 38a and the upper face of a rotor 38a next below. The coupling together for unitary rotation thereof of each rotor with an adjacent spacer can be as depicted in FIG. 12.

Next, a spacer 60' is loosely mounted on the shaft 24M it being lowered into contact at its bottom face with the upper face of the mounted rotor 38a, engagement of coupling projections and passages on these components being effected. Next a second rotor 38a is slid into the shaft with its lower face placed in contact with the upper end of the spacer 60' and projection/spacer engagement as seen in FIG. 11 established. Two more spacers and rotors are mounted in sequence in like manner until at the top of the assembly, the upper face of the topmost rotor is in position to have a locknut 62 screwed onto a threaded upper part of the shaft so as to hold the longitudinal assemblage of spacers and rotors in urged together relationship on the drive shaft.

Where shorter length spacers are used in the assembly and if a space exists between the top face of the uppermost rotor as to preclude longitudinal urging together of the rotors and spacers so mounted, an additional spacer to compensate for this will be used, and the locknut will engage said additional spacer in effecting the required urging together of the assembled components.

With the assembly thus completed, baskets or holding frames could be mounted on the rotors. The assembly can then be lifted (with a hoist) and carried to the concentrator where it is mounted onto the base following which the sample vessel holders (containing samples) can be loaded in the baskets. The concentrator is now set for carrying on with sample drying.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A centrifugal vacuum concentrator for concentrating liquid samples contained in sample vessels comprising:
   a base;
   a rotor assembly mounted on said base, said rotor assembly including a drive shaft upright and rotatable on the base about a fixed axis, a plurality of rotors carried on the drive shaft spaced one above another each at a corresponding one of a plurality of locations above said base;

sample vessel holding structure carried on each rotor;

a cover receivable on said base, said cover having a closed position wherein it surroundingly encloses said rotor assembly and defines with said base an operating chamber, said cover in closed position being engaged with said base such as to establish an air excluding seal of the operating chamber with respect to an outside air environment, said cover having an open position wherein the cover is disengaged from said base unit and unobstructedly located relative to the base such that alongside at rotor level access is user available from locations in each of four quadrants of an imaginary circle the center of which lies on said fixed axis for mounting and demounting sample vessels from said rotor sample vessel holding structure; and means for communicating said operating chamber with a source of vacuum, said cover being moveable to an open position by elevating said cover a distance upwardly from said base; and means connected to said cover for moving it between cover closed and cover open positions and vice versa, said cover moving means comprising an elevator unit, the elevator unit having an upwardly and downwardly traveling part fixed to said cover.

2. A centrifugal vacuum concentrator in accordance with claim 1 in which said elevator is operable to elevate said cover to an open position wherein a lowermost structural part of the cover locates above a location of any sample vessel held in the sample vessel holder structure of an uppermost rotor in the rotor assembly.

3. A centrifugal vacuum concentrator in accordance with claim 1 in which the means for communicating the operating chamber with a source of vacuum includes a vacuum connect fitting carried at a top surface part of the base and open to the operating chamber, said vacuum connect fitting being in communication with said source of vacuum.

4. A centrifugal vacuum concentrator in accordance with claim 3 in which the source of vacuum is a vacuum pump carried in the base, an inlet to the pump being connected with said vacuum connect fitting.

5. A centrifugal vacuum concentrator in accordance with claim 1 in which a fume removal hose is connected to a top part of the cover for removing fumes liberated incident concentration from the operating chamber.

6. A centrifugal vacuum concentrator in accordance with claim 1 comprising heater means for heating said operating chamber during a sample concentration operation.

7. A centrifugal vacuum concentrator in accordance with claim 6 in which said heater means includes heaters carried exteriorly on a wall structure of said cover at vertical spaced locations thereon.

8. A centrifugal vacuum concentrator in accordance with claim 7 in which said heaters extend in an encircling course around said wall structure.

9. A centrifugal vacuum concentrator in accordance with claim 6 in which said heater means includes at least one vertically aligned row of lamp heaters carried on said cover wall structure.

10. A centrifugal vacuum concentrator in accordance with claim 6 in which said cover has a top head, said heater means including at least one heater carried in said top head.

11. A centrifugal vacuum concentrator in accordance with claim 1 in which said base includes drive means for rotatably driving said drive shaft.

12. A centrifugal vacuum concentrator in accordance with claim 11 in which the rotors carried on said drive shaft are received loosely thereon, each lower rotor in the assembly being spaced from a rotor next above by a spacer received loosely on said drive shaft, and means for coupling each rotor and spacer with said drive shaft for rotation in unison with said drive shaft.

13. A centrifugal vacuum concentrator in accordance with claim 12 in which the coupling means includes coupling structure carried on each rotor cooperatively engagable with coupling structure on a spacer adjacent therewith for drivingly coupling together said each said rotor and adjacent spacer.

14. A centrifugal vacuum concentrator in accordance with claim 13 in which the drive means includes a drive output member, coupling structure on a lowermost rotor in the rotor assembly being engagable with coupling structure on said drive output member to transmit rotary drive to the rotor assembly through said lowermost rotor.

15. A centrifugal vacuum concentrator in accordance with claim 14 in which the coupling structure on each rotor and a spacer adjacent therewith includes a projection on one and a bore passage on another for reception of the projection.

16. A centrifugal vacuum concentrator in accordance with claim 15 in which the projection is carried on the rotor and the bore passage is in the spacer.

17. A centrifugal vacuum concentrator in accordance with claim 15 in which each rotor carries a projection at each of two opposite faces thereof, each spacer having a bore passage at each of opposite ends thereof.

18. A centrifugal vacuum concentrator in accordance with claim 14 in which the coupling structure on the lowermost rotor in the rotor assembly and said drive output member includes a projection on one and a bore passage on a other for reception of the projection.

19. A centrifugal vacuum concentrator in accordance with claim 18 in which the projection is on the rotor and the bore passage is in the drive output member.

20. A centrifugal vacuum concentrator in accordance with claim 11 which the drive means for rotatably driving the drive shaft is a variable drive speed means.

21. A centrifugal vacuum concentrator in accordance with claim 20 in which the drive means is a variable speed electric drive motor.

22. A centrifugal vacuum concentrator in accordance with claim 1 in which said rotor sample vessel holding structure includes at least one holding frame removably fixable to each rotor, the holding frame removably mounting at least one sample vessel holder selected from a family of sample vessel holders of differing vessel number and vessel size capacities.

23. A centrifugal vacuum concentrator in accordance with claim 22 comprising a plurality of at least two holding frames removably fixable to each rotor, plural ones of the holding frames on each rotor being uniformly circularly spaced on said each rotor about a center of the rotor.

24. A centrifugal vacuum concentrator in accordance with claim 1 in which a first end of said drive shaft is bearing guided at said base, a second opposite end of said drive shaft being bearing guided with a bearing carried at an inner side of a top head of said cover, said drive shaft opposite end freely inserting in and removing from said bearing during respective closing and opening movements of said cover.

25. A centrifugal vacuum concentrator in accordance with claim 24 in which the bearing carried in said cover top head is a self-centering bearing.

26. A centrifugal vacuum concentrator in accordance with claim 1 in which the cover has a circular cross section.

27. A centrifugal vacuum concentrator in accordance with claim 1 in which the rotors carried on the drive shaft are spaced one from another on the drive shaft with spacers intervening and engaging with an upper face of a each rotor in the plurality and a lower face of a rotor next above.

28. A centrifugal vacuum concentrator in accordance with claim 27 in which the spacers are of a common length set of such spacers selected from a family of differing common length sets of spacers.

29. A centrifugal vacuum concentrator in accordance with claim 28 in which the spacers in each common length set are color coded in a color different than colors with which others of differing common length sets of spacers are colored.

30. A centrifugal vacuum concentrator in accordance with claim 1 in which said cover includes at least one viewing window therein.

31. A centrifugal vacuum concentrator in accordance with claim 30 in which a strobe light device is carried at the interior of the cover and positioned to project onto sample vessels carried on the rotor assembly so that an observer can visually ascertain a sample volume indicative level of samples carried in said sample vessels through said viewing window.

32. A centrifugal vacuum concentrator in accordance with claim 1 in which a detector is carried on one of said base and operable to interdict a movement of the cover from open to closed position when an object lies across a path of said cover movement.

33. A centrifugal vacuum concentrator in accordance with claim 1 in which access to sample holding structure of each rotor when the cover is in open position is available to a user from four quadrants around the axis of the drive shaft.

34. A centrifugal concentrator in accordance with claim 33 in which access to the sample holding structure is in a circular course of at least about 330 degrees around said axis.

35. A centrifugal vacuum concentrator for concentrating liquid samples contained in sample vessels comprising:
a base;
a rotor assembly mounted on said base, said rotor assembly including a drive shaft upright and rotatable on the base about a fixed axis, a plurality of rotors carried on the drive shaft spaced one above another each at a corresponding one of a plurality of locations above said base;
sample vessel holding structure carried on each rotor;
a cover receivable on said base, said cover having a closed position wherein it surroundingly encloses said rotor assembly and defines with said base an operating chamber, said cover in closed position being engaged with said base such as to establish an air excluding seal of the operating chamber with respect to an outside air environment, said cover having an open position wherein the cover is disengaged from said base unit and unobstructedly located relative to the base such that alongside at rotor level access is available from locations in each of four quadrants of an imaginary circle the center of which lies on said fixed axis for mounting and demounting sample vessels from said rotor sample vessel holding structure;
means for communicating said operating chamber with a source of vacuum; and
heater means for heating said operating chamber during a sample concentration operation, said heater means comprising at least one heater carried in said base effective to heat a top surface of said base.

36. A centrifugal vacuum concentrator in accordance with claim 35 in which said heater extends in an encircling course in said base.

37. A modular structured rotor assembly for mounting to a drive unit of a centrifugal concentrator comprising:
a drive shaft;
a plurality of rotors loosely received on the drive shaft and spaced along the shaft at a succession of rotor locations;
tubular spacers loosely received on the shaft and intervening a face of a rotor in the succession and an opposed face of a rotor next following in the succession with each of opposed ones of a spacer ends in contact with said face and opposed face, said spacers being ones of a set of commom length spacers selected from a family of differing common length sets of spacers, the spacers of one common length set of spacers being color coded in a color different than colors with which others of said differing common length sets of spacers are colored;
means for holding the rotors and spacers in urged together relationship on said drive shaft as a longitudinal assemblage; and
coupling means for unitarily coupling together each spacer and rotor to the drive shaft for effecting rotation of said spacers and rotors in unison with said drive shaft.

38. A modular structured rotor assembly in accordance with claim 37 in which an end of said drive shaft is configured to be removably received in a base drive unit in driving relationship with a rotary drive output member of said base drive unit.

39. A modular structured rotor assembly in accordance with claim 37 in which each rotor carries structure for mounting vessels containing liquid sample thereon.

40. A modular structured rotor assembly in accordance with claim 37 in which the means for holding the rotors and spacers in urged together relationship includes a stop fixed at, at least one end of, said drive shaft.

41. A modular structured rotor assembly in accordance with claim 40 in which the coupling means for coupling together each spacer and rotor to the drive shaft includes projections on said rotors, and bore passages on said spacers in which said projections are received for establishing driving relationship therebetween, said spacers having annular flanges at each of opposite spacer ends, said bore passages being in said flanges.

42. A modular structured rotor assembly in accordance with claim 41 in which said coupling means includes a member on said stop cooperable with the projections carried on a rotor proximal said stop for transmitting rotation to said rotors and said spacers when said drive shaft rotates.

43. A modular structured rotor assembly in accordance with claim 37 in which each of the rotors comprises plural pairs of parallel spaced apart support arms, the pairs of support arms being arrayed symmetrically about a fixed rotation axis of the drive shaft, the support arms of each pair cooperating to define a cradle for reception of a sample vessel holding means.

44. A modular structured rotor assembly in accordance with claim 43 in which the sample vessel holding means is pivotably mounted on said support arms.

* * * * *